(12) United States Patent
Kim et al.

(10) Patent No.: US 11,361,524 B1
(45) Date of Patent: Jun. 14, 2022

(54) SINGLE FRAME CONTROL VIEW

(71) Applicant: DENTSPLY SIRONA INC., York, PA (US)

(72) Inventors: Hong Keun Kim, Frankfurt am Main (DE); Anders Adamson, Darmstadt (DE); Ole Jakubik, Hockenheim (DE); Frederike Franke, Darmstadt (DE)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 17/211,922

(22) Filed: Mar. 25, 2021

(51) Int. Cl.
G06T 19/20 (2011.01)
G06T 17/00 (2006.01)
G16H 50/50 (2018.01)
G06N 20/00 (2019.01)

(52) U.S. Cl.
CPC .............. *G06T 19/20* (2013.01); *G06N 20/00* (2019.01); *G06T 17/00* (2013.01); *G16H 50/50* (2018.01); *G06T 2200/24* (2013.01); *G06T 2210/41* (2013.01); *G06T 2219/004* (2013.01); *G06T 2219/2012* (2013.01)

(58) Field of Classification Search
CPC ..... G06T 19/20; G06T 17/00; G06T 2200/24; G06T 2210/41; G06T 2219/004; G06T 2219/2012; G06T 19/00; G06T 2207/20116; G06T 2207/30168; G06T 2219/2004; G16H 50/50; G06N 20/00; A61C 9/0053; A61C 13/0004; A61B 6/469; A61B 6/5223
See application file for complete search history.

(56) References Cited

U.S. PATENT DOCUMENTS

| 10,390,913 | B2 | 8/2019 | Sabina | |
| 10,888,400 | B2 | 1/2021 | Elbaz | |
| 2016/0051345 | A1* | 2/2016 | Levin | A61B 1/00045 |
| | | | | 433/29 |
| 2019/0231490 | A1* | 8/2019 | Sabina | A61B 1/0646 |

FOREIGN PATENT DOCUMENTS

| EP | 1979877 B1 | 2/2018 |
| EP | 2164424 B1 | 2/2019 |

* cited by examiner

*Primary Examiner* — Xilin Guo
(74) *Attorney, Agent, or Firm* — Dentsply Sirona Inc.

(57) ABSTRACT

The quality of digital impressions geometry and color but also fluorescence, transillumination, reflection and absorption properties can be inferior to single frame 2D/3D images e.g. due to averaging effects, rendering effects, difficult scanning situation etc. This can lead to difficulties in the dental workflow such as the creation of a preparation margin line or detection of diseases such as caries. By providing a correlated view of high-quality single frame images and corresponding 3D models, the dental workflow can be guided to be completed more efficiently using the single frame images.

17 Claims, 11 Drawing Sheets

SINGLE FRAME CONTROL VIEW

TECHNICAL FIELD

The present invention relates generally to a method, system, and computer program product for displaying single frame views of a dental cavity. More particularly, the present invention relates to a method, system, and computer program product for using high quality single frame views of teeth in a dental cavity to generate views that preserve the quality of a view of a tooth in order to aid in dental workflow processes such as the creation of tooth margin lines.

BACKGROUND

A practice in dentistry is to trace the margins of a tooth in a dental software to generate a good restoration fit in a dental procedure. The tracing usually starts by indicating an edge where the margin line is. Using an input device, points on the margin line are sequentially placed. These points are editable and can be placed around the tooth until a fill circle of placed points is created.

In a further step, a line representing the margin line is automatically computed using the points. Said line is editable and can be modified using the input device. Adjusting the placed points adjusts the margin line and additional points can be added to adjust the margin line.

BRIEF SUMMARY

The illustrative embodiments provide a method, system and computer program product for displaying high quality single frame views of teeth in a dental cavity through the use of images that preserve the quality of a view of a tooth in order to aid in dental workflows such as the creation of tooth margin lines or caries detection.

In an aspect herein, a method of providing single frame control view is disclosed. The method includes obtaining data about a dental jaw, or oral cavity, the data including a first virtual 3D model of the dental jaw, and at least one direct measurement data (e.g. single frame 2D and single frame 3D images) that is representative of at least a portion of the first virtual 3D model. An indexing step follows wherein an indexing module is used to index, the data by linking each of one or more perspectives of the first virtual 3D model to a corresponding direct measurement data indicative of said one or more perspectives in order to establish a control between them and to provide a paired listing of first virtual 3D model perspectives and corresponding single frame images. Responsive to the indexing, a selection step follows wherein a pair from the paired listing is selected for display and an operator input is provided on a direct measurement data of the selected pair to compute, using a proposal generator, a modification in the first virtual 3D model of the selected pair indicative of the operator input. In this method, the computed modification produces a second virtual 3D model that is more accurate than an accuracy of the first virtual 3D model.

The virtual 3D model comprises the 3D-geometry information along with additional information complementing it such as texture, visual color, fluorescence information, absorption information, transillumination information, reflection information, margin information e.g. a manually or automatic generated line, caries information depicted e.g. as one or more colors or lines, or any other manually generated or automatically proposed information that can be visualized or displayed as part of the model, within the model, on the surface of the model, or as a complement to the geometry of the model such as textboxes, arrows, legends, crosshairs, points, circles.

A change, modification or recalculation in any of the displayed features or the underlying numerical calculations of any portion of the above mentioned 3D model such as a modified geometry, a modified color, a modified texture, a modified margin proposal, a modified caries proposal, a modified geometry object, a modified position of the crosshair, a modification of any other diagnostical feature or graphical information together with the model, a modified fluorescence information, a modified absorption information, a modified transillumination information, a modified reflection information is regarded as newly produced or recalculated 3D model that results in a second virtual 3D model that is more accurate than an accuracy of the first virtual 3D model.

In another aspect herein, any combination of the following is disclosed: the at least one direct measurement data is a 2D image (such as 2D color, 2D fluorescence, 2D infrared, 2D caries, 2D absorption, 2D reflection and 2D transillumination images) that provides information about an unmodified texture, color of the dental jaw, fluorescence, transillumination, reflection or absorption properties of the dental jaw; the at least one direct measurement data is a 3D image that provides information about an unmodified geometry of the dental jaw (for example, with or without color, texture, caries, infrared, absorption, reflection, transillumination or fluorescence mapping); the computed modification is a change in geometry or color of a part of the first virtual 3D model; the computed modification is a change in a proposed margin of the first virtual 3D model; the paired listing is displayed as a mapping on the first virtual 3D model; the paired listing is displayed as a table or list; the control is a bi-directional display relationship and selecting one member of the pair causes another member of the pair to be displayed; the computed modification is displayed in real-time; another input is provided on the first or second virtual 3D model and a corresponding live or delayed feedback is provided on a corresponding position on the direct measurement data; the operator input that is provided on a first location of the direct measurement data of the selected pair causes a computation, using the proposal generator, of the modification in a corresponding location on the first virtual 3D model to produce the second virtual 3D model, and the proposal generator is a machine learning model.

In yet another aspect, a method is disclosed that includes obtaining data about a dental jaw, the data including a first virtual 3D model of the dental jaw, and at least one direct measurement data that corresponds to at least a portion of the first virtual 3D model; indexing, by an indexer, the data by linking each of one or more perspectives of the first virtual 3D model with a corresponding direct measurement data indicative of said one or more perspectives in order to establish a control between them and to provide a paired listing of first virtual 3D model perspectives and corresponding single frame images; selecting, responsive to the indexing, a pair from the paired listing in order to display a first direct measurement data of the at least one direct measurement data and the first virtual 3D model oriented at a first orientation corresponding to the first direct measurement data; providing operator input on a first location of the first virtual 3D model data of the selected pair to compute a corresponding location on the first direct measurement data for displaying a direct measurement data tool, wherein the direct measurement data tool is configured for a viewing or measurement operation that are more accurate than a viewing or measurement operation of the first virtual 3D model. In the method, the at least one direct measurement data is a 2D image or a 3D image.

In a further aspect, a computer system is disclosed. The computer system includes a processor configured to perform the steps including: obtaining data about a dental jaw, the data including a first virtual 3D model of the dental jaw, and at least one direct measurement data used that is representative of at least a portion of the first virtual 3D model; indexing, by an indexer, the data by linking each of one or more perspectives of the first virtual 3D model with a corresponding direct measurement data indicative of said one or more perspectives in order to establish a control between them and to provide a paired listing of first virtual 3D model perspectives and corresponding single frame images; selecting, responsive to the indexing, a pair from the paired listing for display; providing operator input on a direct measurement data of the selected pair to compute, using a proposal generator, a modification in the first virtual 3D model of the selected pair indicative of the operator input; wherein the computed modification produces a second virtual 3D model that is more accurate than an accuracy of the first virtual 3D model.

Another computer system comprising a processor is also disclosed and is configured to perform the steps including: obtaining data about a dental jaw, the data including a first virtual 3D model of the dental jaw, and at least one direct measurement data that is representative of at least a portion of the first virtual 3D model; indexing, by an indexer, the data by linking each of one or more perspectives of the first virtual 3D model with a corresponding direct measurement data indicative of said one or more perspectives in order to establish a control between them and to provide a paired listing of first virtual 3D model perspectives and corresponding single frame images; selecting, responsive to the indexing, a pair from the paired listing in order to display a first direct measurement data of the at least one direct measurement data and the first virtual 3D model oriented at a first orientation corresponding to the first direct measurement data; providing operator input on a first location of the first virtual 3D model data of the selected pair to compute a corresponding location on the first direct measurement data for displaying a direct measurement data tool, wherein the direct measurement data tool is configured for a viewing or measurement operation that are more accurate than a viewing or measurement operation of the first virtual 3D model.

A non-transitory computer-readable storage is also disclosed. The non-transitory computer readable medium stores a program which, when executed by a computer system, causes the computer system to perform a procedure comprising: obtaining data about a dental jaw, the data including a first virtual 3D model of the dental jaw, and at least one direct measurement data that is representative of at least a portion of the first virtual 3D model; indexing, by an indexer, the data by linking each of one or more perspectives of the first virtual 3D model with a corresponding direct measurement data indicative of said one or more perspectives in order to establish a control between them and to provide a paired listing of first virtual 3D model perspectives and corresponding single frame images; selecting, responsive to the indexing, a pair from the paired listing for display; providing operator input on a direct measurement data of the selected pair to compute, using a proposal generator, a modification in the first virtual 3D model of the selected pair indicative of the operator input; wherein the computed modification produces a second virtual 3D model that is more accurate than an accuracy of the first virtual 3D model.

Another non-transitory computer-readable storage medium is disclosed. It stores a program which, when executed by a computer system, causes the computer system to perform a procedure comprising: obtaining data about a dental jaw, the data including a first virtual 3D model of the dental jaw, and at least one direct measurement data that corresponds to at least a portion of the first virtual 3D model; indexing, by an indexer, the data by linking each of one or more perspectives of the first virtual 3D model with a corresponding direct measurement data indicative of said one or more perspectives in order to establish a control between them and to provide a paired listing of first virtual 3D model perspectives and corresponding single frame images; selecting, responsive to the indexing, a pair from the paired listing in order to display a first direct measurement data of the at least one direct measurement data and the first virtual 3D model oriented at a first orientation corresponding to the first direct measurement data; providing operator input on a first location of the first virtual 3D model data of the selected pair to compute a corresponding location on the first direct measurement data for displaying a direct measurement data tool, wherein the direct measurement data tool is configured for a viewing or measurement operation that are more accurate than a viewing or measurement operation of the first virtual 3D model.

In an aspect herein, coordinate transforms are assigned to 2D (color, fluorescence, infrared) images (or single frame 3D data/3D data frames) to generate a corresponding set of allowed, discrete orientations of an associated 3D model in order to enable quick and direct user access of the working view (same perspective and size for 3D model and 2D (color, fluorescence, infrared) image). User-manipulated, user-weighted single or multiple 2D (color, fluorescence, infrared) images/3D data frames are further used as input data for automated workflow proposals after model reconstruction. Live or delayed feedback for workflows such as drawing of margins are enabled as well as simultaneous control and modification of a complete margin proposal.

Illustrative embodiments herein are advantageous for allowing an operator to use unaveraged and direct raw 2D images (color, fluorescence, infrared) and 3D data frames (geometry) to provide user input on direct raw 2D images and 3D data frames for AI (Artificial Intelligence)/ML (Machine Learning) algorithms concerning a workflow (e.g. margin proposal)—these user inputs are directly implemented in the current proposal e.g. triggering a recalculation of the proposal.

Illustrative embodiments herein also allow operator input concerning selection of a subset of 2D (color, fluorescence, infrared) images/3D data frames, which are specifically weighted, included or excluded in the current workflow proposal (e.g. operator input can trigger a recalculation of the proposal to incorporate said operator input). Further, illustrative embodiments index images for navigation and in addition allow the provision of operator input concerning raw 2D images and 3D data frames to train AI algorithms to weight, include or exclude selected images.

Even further, illustrative embodiments are advantageous for helping in various diagnostic and therapeutic workflows. Examples are the display of characters on dental materials and tools such as scanbodies, abutments, aligners or other identification features. Embodiments also help in detection, communication, visualization, assessment and treatment of dental diseases such as periodontal disease, oral cancer, tooth decay, tooth erosion, caries detection, discoloration and orthodontic diseases. The processes described herein are further transferable to any other dental workflow and procedure that integrates a digital impression and requires higher quality and accuracy in texture, color and 3D information than a corresponding rendered 3D model. In an example, the quality and/or accuracy exceeds at least a threshold quality and/or accuracy. The dental workflows include dental workflows and indications concerning, for example, periodontal disease, oral cancer, tooth decay, tooth erosion, caries detection, discoloration, orthodontic diseases, or otherwise dental workflows in which a plurality of images of an intraoral scanner are rendered into a combined object e.g. a 3D model, a colored texture map on the 3D model, rendered information of 2D-Fluorescence and IR images mapped to the 3D model etc. Therefore the term 2D image, besides the 2D images commonly known as colored photographic pictures in the visible light spectrum may also refer to 2D images which contain information which are generated with the addition of light sources in the invisible spectrum such as fluorescence, transillumination or absorption properties via ultraviolet (UV) or infrared (IR) radiation. Thus, the term 2D image or direct measurement data (such as single frame 3D images) besides referring to colored 2D images also refers to 2D fluorescence images and 2D infrared images but is not limited to these. These images can, for example, be utilized to detect caries.

Higher quality or accuracy used herein refers to a closer representation of the parts of acquired data to the properties of the real scanned object or ground truth. For color a higher quality or a higher accuracy is given by a closer representation of the true color of the scanned object. As an example, the color of a point of the scanned surface can be expressed by values in a color space such as the CIELAB color space. Smaller deviations in the $L\_i*a\_i*b\_i$ values obtained from an intraoral scanner when compared to the true $L\_r*a\_r*b\_r$ values of the real imaged object therefore correspond to a higher quality and accuracy in color (i=intraoral scanner, r=real or reference). For 3D data a higher quality or a higher accuracy is given by a closer representation of the 3-dimensional surface of the scanned object e.g. the tooth margin. As an example, 3D information of a surface can be expressed as 3D coordinates x,y,z in space. Thus a point of the scanned surface with its coordinate $x_i, y_i, z_i$ obtained by an intraoral scanner is more accurate when it has a smaller deviation from the true $x_r, y_r, z_r$ of the object in the same coordinate system. For data acquired by additionally utilizing UV or IR radiation a higher quality or accuracy is given by information which is in closer resemblance to the true behavior of the illuminated object in terms of wavelength and intensity ultimately resulting again in visible 2D black/white, grayscale or color images. However, these effects depend on the specific application and the underlying physical and optical processes.

Thus unlike in conventional approaches, operator input is provided for AI and automated proposals, direct access to a working view is provided by manipulation of a rendered 3D model—thus providing a same perspective and size for the rendered 3D model and a 2D (color, fluorescence, infrared) image/2D (color, fluorescence, infrared) image, single frame 3D data are incorporated in a working view, color information in 2D (color, fluorescence, infrared) images is utilized for a workflow and bi-directional control of 3D models and corresponding single frame images are provided.

BRIEF DESCRIPTION OF THE DRAWINGS

Certain novel features believed characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

DETAILED DESCRIPTION

Figure 1:
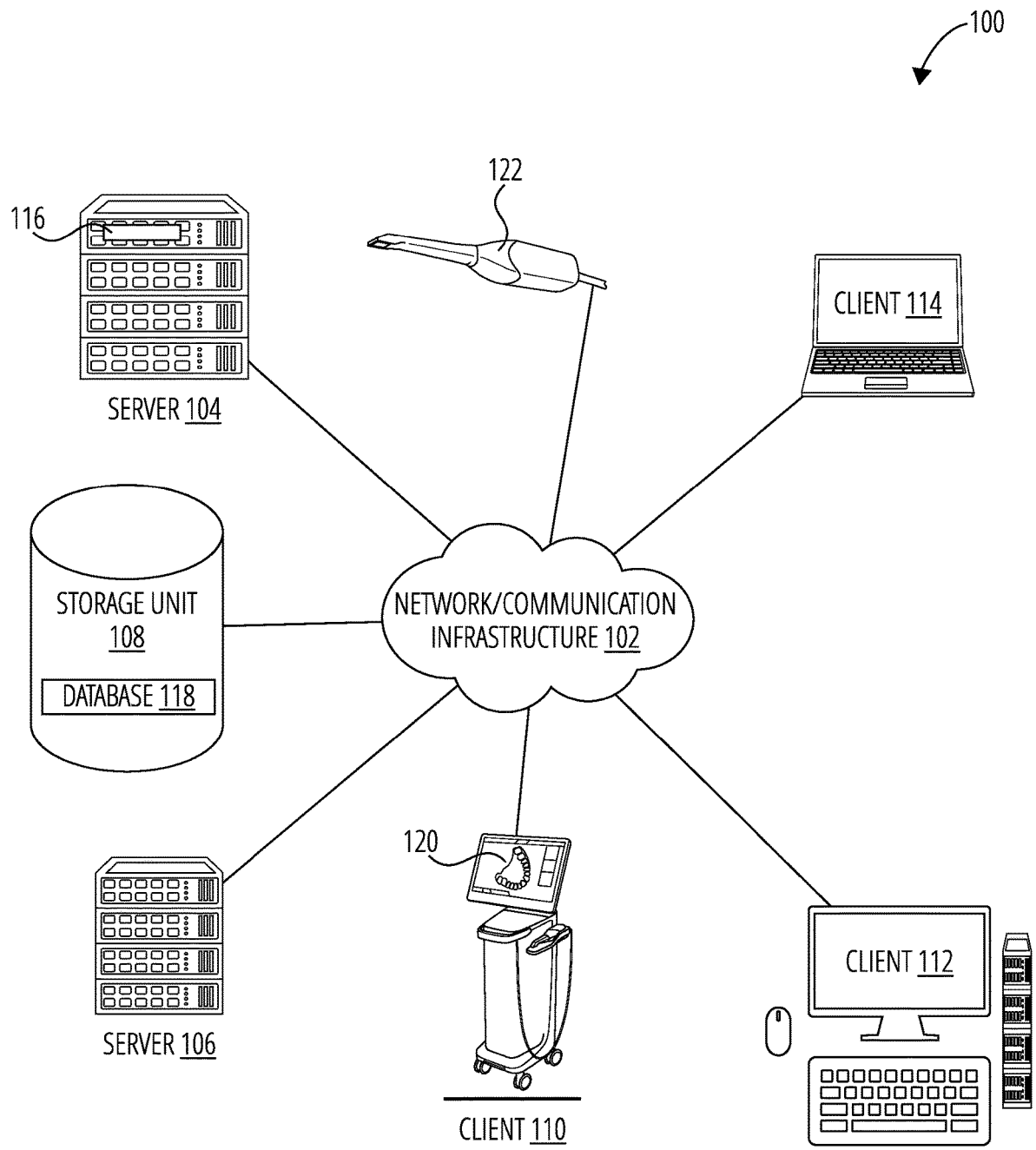
FIG. 1 depicts a block diagram of a network of data processing systems in which illustrative embodiments may be implemented.

The illustrative embodiments recognize that the quality of digital impressions geometry and color is usually inferior to the quality of single frame 2D/3D images due to, for example, averaging effects, rendering effects, difficult scanning situation etc. This can lead to difficulties in dental workflows such as the manual or automatic drawing of a preparation margin line.

The illustrative embodiments also recognize that the geometry and texture of dental 3D models are generated by a plurality of single images and despite advances in the field, there are significant quality differences between the texture/accuracy of the digital impression or 3D model and that of the physical teeth. These difficulties are significantly exacerbated by challenging situations including but not limited to presence of blood and saliva, epigingival preparation margins with retraction cord, small structures/pores, bridging effects, complex geometries, and highly reflective, translucent surfaces as well as glare. In a generated/calculated 3D model, the geometry and color of the model is usually calculated from a variety of single frames (e.g. 2D photos or single 3D frames) which calculation introduces averaging effects in the 3D model. Further conventional machine learning models use 3D models having said averaging effects to create automated margin lines which propagates the averaging errors throughout the margin line creation process. By using single frames which contain more information/details about a subjection tooth, a truer description of the tooth can be obtained for margin line creation.

The illustrative embodiments recognize that the presently available tools or solutions do not address these needs or provide adequate solutions for these needs. The illustrative embodiments used to describe the invention generally address and solve the above-described problems and other problems related to providing a single frame live or non-concurrent control view to an operator.

An embodiment can be implemented as a software and/or hardware application. The application implementing an embodiment can be configured as a modification of a dental system, as a separate application that operates in conjunction with an existing dental system, a standalone application, or some combination thereof.

Particularly, some illustrative embodiments provide a method that utilizes single frame 2D images (e.g. photos) or 3D images (e.g. point clouds) to support a manual and automatic generation of margin lines. Though margin line creation is generally discussed, it is not intended to be limiting and other 3D model modification or display workflows through the use of single images including geometry and color modifications which are concurrent or non-concurrent are possible. This includes workflows that integrate a digital impression and require higher quality and accuracy in texture, color and 3D information than a quality of the corresponding rendered 3D model, for example, in the detection, communication, visualization, assessment and treatment of dental diseases such as periodontal disease, oral cancer, tooth decay, tooth erosion, caries, discoloration and orthodontic diseases. An operator may provide input on single frame images (such as for caries detection or margin line preparation) to guide an automated proposal. The operator input may include: a plurality of points on the single frame along the margin, drawn line along the margin, selection and weighting of one or more single frame images, operator input on single frame images to train the automated proposal of margins. In another example, an operator provides input on single frame images to train a model for an automated proposal. The operator input may include: a plurality of points on the single frame along the margin, drawn line along the margin, selection and weighting of one or more single frame images, operator input on single frame images to train the automated proposal of margins.

In another illustrative embodiment, an easy to use environment is provided for the operator input. Said environment comprises a working/correlated view wherein a same perspective of the generated/rendered 3D model and single frame 2D or 3D images (photos, point-clouds) are shown. For example, a same orientation and zoom factor of the single frame images are shown. In another embodiment, an access to the working view may be provided via indexing, mapping and navigation tools as described hereinafter.

Further, a control tool that is preferably live, such as a crosshair is provided to assess whether the position of a displayed feature such as a drawn margin line, or any other displayed feature within the oral cavity such as teeth, gingiva, dental materials and diseases, is correct. This feedback option may be realized in the working view and when a margin line is drawn on the 3D model, the position of the crosshair on the single frame concurrently or at another time serves as a feedback for whether the position is correct. Thus, a user may engage and modify the 3D model and a crosshair may appear on the single frame (and optionally on the 3D model) for position control. Alternatively, the user may engage and modify the single frame and a crosshair may appear on the 3D model (and optionally on the single frame) for position control. In these embodiments, the operator input may be provided simultaneously for a given region e.g. a partial or complete margin of a preparation.

The illustrative embodiments are described with respect to certain types of scanners such as dental scanner 122 which may be used to obtain images for generation of the 3D model, as well as with respect to certain workflows such as margin line preparations but are not intended to be limited to them. A client 110 with a client application 120 may be used to render or generate 3D models from single frames. Said client application 120 may also be configured to perform part or all the steps discussed herein.

The illustrative embodiments are described with respect to other scenes, subjects, measurements, devices, data processing systems, environments, components, and applications only as examples. Any specific manifestations of these and other similar artifacts are not intended to be limiting to the invention. Any suitable manifestation of these and other similar artifacts can be selected within the scope of the illustrative embodiments.

Furthermore, the illustrative embodiments may be implemented with respect to any type of data, data source, or access to a data source over a data network. Any type of data storage device may provide the data to an embodiment of the invention, either locally at a data processing system or over a data network, within the scope of the invention. Where an embodiment is described using a mobile device, any type of data storage device suitable for use with the mobile device may provide the data to such embodiment, either locally at the mobile device or over a data network, within the scope of the illustrative embodiments.

The illustrative embodiments are described using specific surveys, code, hardware, algorithms, designs, architectures, protocols, layouts, schematics, and tools only as examples and are not limiting to the illustrative embodiments. Furthermore, the illustrative embodiments are described in some instances using particular software, tools, and data processing environments only as an example for the clarity of the description. The illustrative embodiments may be used in conjunction with other comparable or similarly purposed structures, systems, applications, or architectures. For example, other comparable mobile devices, structures, systems, applications, or architectures therefore, may be used in conjunction with such embodiment of the invention within the scope of the invention. An illustrative embodiment may be implemented in hardware, software, or a combination thereof.

The examples in this disclosure are used only for the clarity of the description and are not limiting to the illustrative embodiments. Additional data, operations, actions, tasks, activities, and manipulations will be conceivable from this disclosure and the same are contemplated within the scope of the illustrative embodiments.

Any advantages listed herein are only examples and are not intended to be limiting to the illustrative embodiments. Additional or different advantages may be realized by specific illustrative embodiments. Furthermore, a particular illustrative embodiment may have some, all, or none of the advantages listed above.

Figure 2:
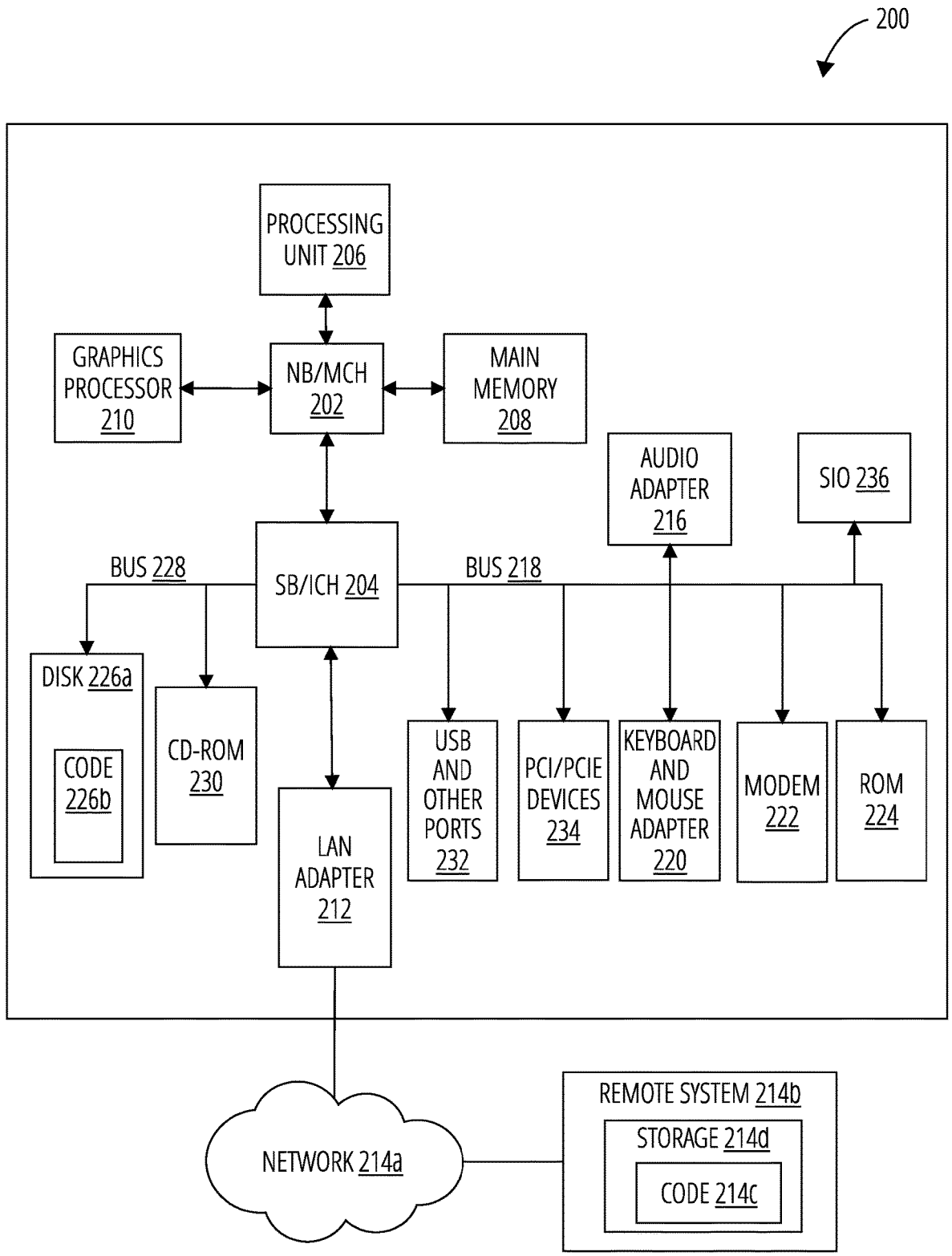
FIG. 2 depicts a block diagram of a data processing system in which illustrative embodiments may be implemented.

With reference to the figures and in particular with reference to FIG. 1 and FIG. 2, these figures are example diagrams of data processing environments in which illustrative embodiments may be implemented. FIG. 1 and FIG. 2 are only examples and are not intended to assert or imply any limitation with regard to the environments in which different embodiments may be implemented. A particular implementation may make many modifications to the depicted environments based on the following description.

FIG. 1 depicts a block diagram of a network of data processing systems in which illustrative embodiments may be implemented. Data processing environment 100 is a network of computers in which the illustrative embodiments may be implemented. Data processing environment 100 includes network/communication infrastructure 102. Network/communication infrastructure 102 is the medium used to provide communications links between various devices, databases and computers connected together within data processing environment 100. Network/communication infrastructure 102 may include connections, such as wire, wireless communication links, or fiber optic cables.

Clients or servers are only example roles of certain data processing systems connected to network/communication infrastructure 102 and are not intended to exclude other configurations or roles for these data processing systems. Server 104 and server 106 couple to network/communication infrastructure 102 along with storage unit 108. Software applications may execute on any computer in data processing environment 100. Client 110, client 112, client 114 are also coupled to network/communication infrastructure 102. Client 110 may be a dental acquisition unit with a display. A data processing system, such as server 104 or server 106, or clients (client 110, client 112, client 114) may contain data and may have software applications or software tools executing thereon.

Only as an example, and without implying any limitation to such architecture. FIG. 1 depicts certain components that are usable in an example implementation of an embodiment. For example, servers and clients are only examples and do not to imply a limitation to a client-server architecture. As another example, an embodiment can be distributed across several data processing systems and a data network as shown, whereas another embodiment can be implemented on a single data processing system within the scope of the illustrative embodiments. Data processing systems (server 104, server 106, client 110, client 112, client 114) also represent example nodes in a cluster, partitions, and other configurations suitable for implementing an embodiment.

Dental scanner 122 includes one or more sensors that measure teeth by obtaining a plurality of images through projections that map a person's oral cavity. In an example, the dental scanner 122 captures data points as often as several thousand times each second, automatically registering the sizes and shapes of each tooth. It continuously sends this data to the connected computer's software, which builds it into a 3D impression of the patient's oral cavity.

A most widely used digital format is the STL (Standard Tessellation Language) format. This format describes a succession of triangulated surfaces where each triangle is defined by three points and a normal surface. STL files may describe only the surface geometry of a three-dimensional object without any representation of color, texture, or other CAD model attributes. However, other file formats have been developed to record color, transparency, or texture of dental tissues (such as Polygon File Format, PLY files). Irrespective of the type of imaging technology employed, scanners or cameras project light that is then recorded as individual images and compiled by the software after recognition of POI (points of interest). For example, two coordinates (x and y) of each point are evaluated on the image, and the third coordinate (z) is then calculated depending on a distance from the scanner.

Client application 120 or any other application 116 implements an embodiment described herein. Client application 120 can use data from dental scanner 122 to generate or render 3D models using single frame images taken by the dental scanner 122. Client application 120 can also obtain data from storage unit 108 for rendering or characterization. Client application 120 can also execute in any of data processing systems (server 104 or server 106, client 110, client 112, client 114), such as client application 116 in server 104 and need not execute in the same system as client 110.

Server 104, server 106, storage unit 108, client 110, client 112, client 114, may couple to network/communication infrastructure 102 using wired connections, wireless communication protocols, or other suitable data connectivity. Client 110, client 112 and client 114 may be, for example, personal computers or network computers.

In the depicted example, server 104 may provide data, such as boot files, operating system images, and applications to client 110, client 112, and client 114. Client 110, client 112 and client 114 may be clients to server 104 in this example. Client 110, client 112 and client 114 or some combination thereof, may include their own data, boot files, operating system images, and applications. Data processing environment 100 may include additional servers, clients, and other devices that are not shown. Server 104 includes an application 116 that may be configured to implement one or more of the functions described herein for displaying a live control view in accordance with one or more embodiments.

Server 106 may include a search engine configured to search stored files such as images and 3D models of patients for a dental practice in response to a request from an operator as described herein with respect to various embodiments.

In the depicted example, data processing environment 100 may be the Internet. Network/communication infrastructure 102 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client-server environment in which the illustrative embodiments may be implemented. A client-server environment enables software applications and data to be distributed across a network such that an application functions by using the interactivity between a client data processing system and a server data processing system. Data processing environment 100 may also employ a service-oriented architecture where interoperable software components distributed across a network may be packaged together as coherent business applications. Data processing environment 100 may also take the form of a cloud, and employ a cloud computing model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

With reference to FIG. 2, this figure depicts a block diagram of a data processing system in which illustrative embodiments may be implemented. Data processing system 200 is an example of a computer, such client 110, client 112, client 114 or s server 104, server 106, in FIG. 1, or another type of device in which computer usable program code or instructions implementing the processes may be located for the illustrative embodiments.

Data processing system 200 is described as a computer only as an example, without being limited thereto. Implementations in the form of other devices, in FIG. 1, may modify data processing system 200, such as by adding a touch interface, and even eliminate certain depicted components from data processing system 200 without departing from the general description of the operations and functions of data processing system 200 described herein.

In the depicted example, data processing system 200 employs a hub architecture including North Bridge and memory controller hub (NB/MCH) 202 and South Bridge and input/output (I/O) controller hub (SB/ICH) 204. Processing unit 206, main memory 208, and graphics processor 210 are coupled to North Bridge and memory controller hub (NB/MCH) 202. Processing unit 206 may contain one or more processors and may be implemented using one or more heterogeneous processor systems. Processing unit 206 may be a multi-core processor. Graphics processor 210 may be coupled to North Bridge and memory controller hub (NB/MCH) 202 through an accelerated graphics port (AGP) in certain implementations.

In the depicted example, local area network (LAN) adapter 212 is coupled to South Bridge and input/output (I/O) controller hub (SB/ICH) 204. Audio adapter 216, keyboard and mouse adapter 220, modem 222, read only memory (ROM) 224, universal serial bus (USB) and other ports 232, and PCI/PCIe devices 234 are coupled to South Bridge and input/output (I/O) controller hub (SB/ICH) 204 through bus 218. Hard disk drive (HDD) or solid-state drive (SSD) 226a and CD-ROM 230 are coupled to South Bridge and input/output (I/O) controller hub (SB/ICH) 204 through bus 228. PCI/PCIe devices 234 may include, for example, Ethernet adapters, add-in cards, and PC cards for notebook computers. PCI uses a card bus controller, while PCIe does not. Read only memory (ROM) 224 may be, for example, a flash binary input/output system (BIOS). Hard disk drive (HDD) or solid-state drive (SSD) 226a and CD-ROM 230 may use, for example, an integrated drive electronics (IDE), serial advanced technology attachment (SATA) interface, or variants such as external-SATA (eSATA) and micro-SATA (mSATA). A super I/O (SIO) device 236 may be coupled to South Bridge and input/output (I/O) controller hub (SB/ICH) 204 through bus 218.

Memories, such as main memory 208, read only memory (ROM) 224, or flash memory (not shown), are some examples of computer usable storage devices. Hard disk drive (HDD) or solid-state drive (SSD) 226a, CD-ROM 230, and other similarly usable devices are some examples of computer usable storage devices including a computer usable storage medium.

An operating system runs on processing unit 206. The operating system coordinates and provides control of various components within data processing system 200 in FIG. 2. The operating system may be a commercially available operating system for any type of computing platform, including but not limited to server systems, personal computers, and mobile devices. An object oriented or other type of programming system may operate in conjunction with the operating system and provide calls to the operating system from programs or applications executing on data processing system 200.

Instructions for the operating system, the object-oriented programming system, and applications or programs, such as application 116 and client application 120 in FIG. 1, are located on storage devices, such as in the form of codes 226b on Hard disk drive (HDD) or solid-state drive (SSD) 226a, and may be loaded into at least one of one or more memories, such as main memory 208, for execution by processing unit 206. The processes of the illustrative embodiments may be performed by processing unit 206 using computer implemented instructions, which may be located in a memory, such as, for example, main memory 208, read only memory (ROM) 224, or in one or more peripheral devices.

Furthermore, in one case, code 226b may be downloaded over network 214a from remote system 214b, where similar code 214c is stored on a storage device 214d in another case, code 226b may be downloaded over network 214a to remote system 214b, where downloaded code 214c is stored on a storage device 214d.

The hardware in FIG. 1 and FIG. 2 may vary depending on the implementation. Other internal hardware or peripheral devices, such as flash memory, equivalent non-volatile memory, or optical disk drives and the like, may be used in addition to or in place of the hardware depicted in FIG. 1 and FIG. 2. In addition, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may comprise one or more buses, such as a system bus, an I1O bus, and a PCI bus. Of course, the bus system may be implemented using any type of communications fabric or architecture that provides for a transfer of data between different components or devices attached to the fabric or architecture.

A communications unit may include one or more devices used to transmit and receive data, such as a modem or a network adapter. A memory may be, for example, main memory 208 or a cache, such as the cache found in North Bridge and memory controller hub (NB/MCH) 202. A processing unit may include one or more processors or CPUs.

The depicted examples in FIG. 1 and FIG. 2 and above-described examples are not meant to imply architectural limitations. For example, data processing system 200 also may be a tablet computer, laptop computer, or telephone device in addition to taking the form of a mobile or wearable device.

Where a computer or data processing system is described as a virtual machine, a virtual device, or a virtual component, the virtual machine, virtual device, or the virtual component operates in the manner of data processing system 200 using virtualized manifestation of some or all components depicted in data processing system 200. For example, in a virtual machine, virtual device, or virtual component, processing unit 206 is manifested as a virtualized instance of all or some number of hardware processing units 206 available in a host data processing system, main memory 208 is manifested as a virtualized instance of all or some portion of main memory 208 that may be available in the host data processing system, and Hard disk drive (HDD) or solid-state drive (SSD) 226a is manifested as a virtualized instance of all or some portion of Hard disk drive (HDD) or solid-state drive (SSD) 226a that may be available in the host data processing system. The host data processing system in such cases is represented by data processing system 200.

Figure 3:
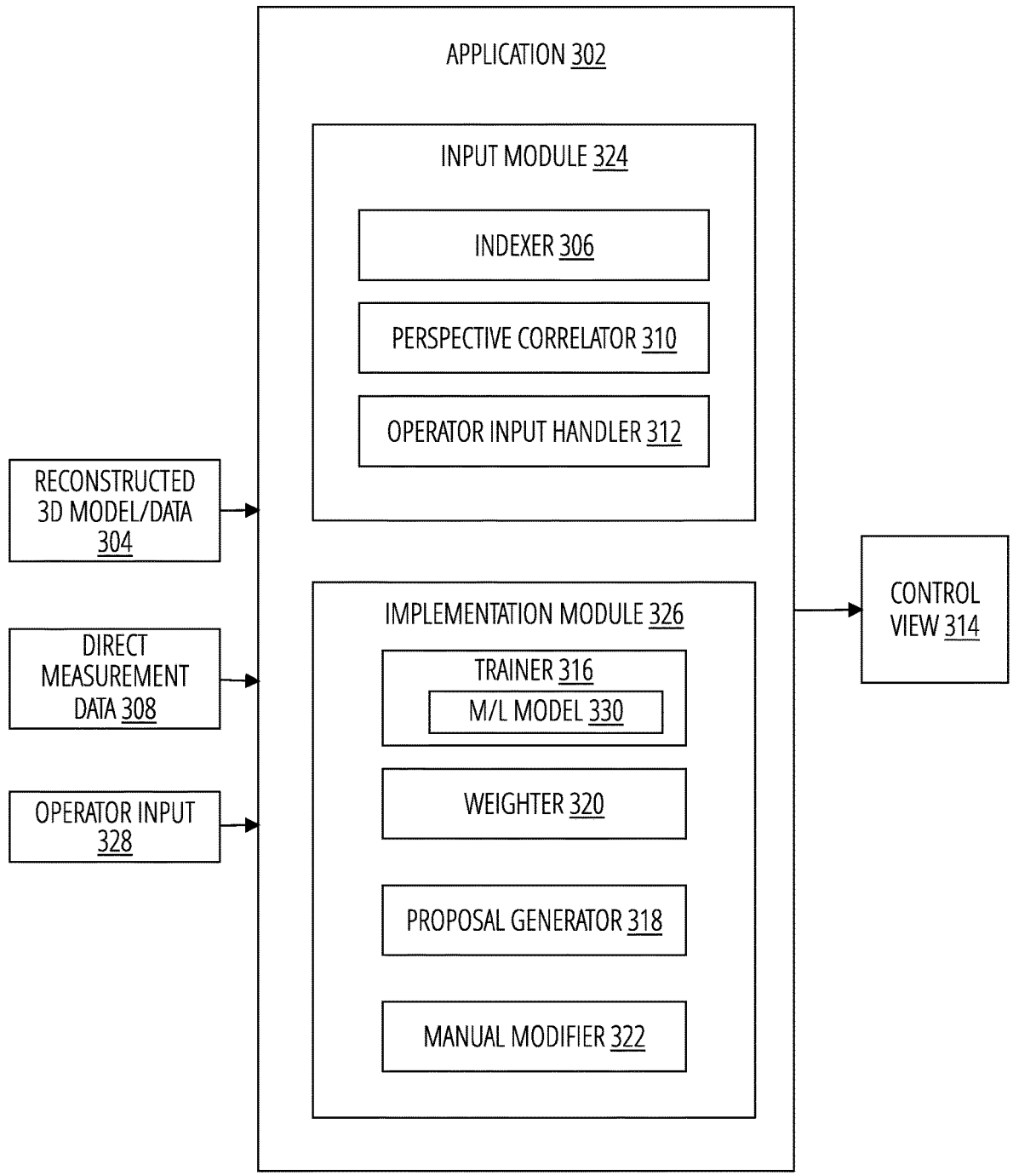
FIG. 3 depicts a block diagram of an application in which illustrative embodiments may be implemented.

Turning now to FIG. 3, an illustrative embodiment shows an application 302 of a data processing system 200 which will now be explained. The application is not meant to be limiting and can be embodied as client application 120, application 116 or any other application in a data processing system 200. Application 302 takes as input, the operator input 328, reconstructed 3D model 304 and direct measurement data 308 that is representative or corresponds to at least a portion of the reconstructed 3D model 304. Application 302 includes one or modules including an input module 324 and an implementation module 326. Input module 324 includes an indexer 306, a perspective correlator 310 and an operator input handler 312 configured to accept and handle the operator input 328. Application 302 displays and updates a control view 314 as output, for example in real time. By taking in direct measurement data 308 (which is unmodified or unaveraged measurement data, for example, compared to a true representation of the physical object by at least by a threshold amount, and generally referred to herein interchangeably as raw data/image, single frame image/data, single frame 2D data/image, single frame 3D data/image, photos, point cloud data, single frame STL and the like), application 302 is able to provide, from the input module 324, one or more of the direct measurement data 308 as input data for the implementation module 326.

In an illustrative embodiment, each of the single frame 3D data of the direct measurement data 308 (i.e. single shot of a measurement volume) has an established coordinate transform with respect to the reconstructed digital model. It is therefore possible to orient the 3D model from a desired perspective (orientation, size) e.g. from a top viewing angle of the scanner (scanner perspective) for a given single 2D photographic image or a 3D data frame. Thus, the number of orientations and perspectives is limited by the number of discrete single frame 3D data. The coordinate transforms for the single frame 3D data may be established by an initial coordinate transform, a sequential registration process wherein single frame images are sequentially registered to each other during a scanning procedure, a non-sequential registration process or an optimization process etc. A coordinate transform in general provides the information for a spatial relationship, usually in 3 dimensions, between two objects which can be expressed e.g. by a translational and rotational transformation. An initial coordinate transform can be determined via algorithms such as the iterative closest point (ICP) method or other calculations and calibration methods e.g. by utilizing known sources of information such as an inertial movement unit, defined and known movement between single frames etc. In a sequential registration process single frames are stitched sequentially. In such a process it is possible to determine the coordinate transform not only between consecutive frames but also to other frames in the sequence. In a sequential registration process also only every i-th frame can be utilized for performance or accuracy reasons.

Moreover, each single frame 2D data such as 2D image (2D video image) from a video may be correlated to a single frame 3D data that was generated directly before or after the single frame 2D data. It is thus possible to assign each single frame 2D data a coordinate transform (relative or absolute coordinate transform).

The establishment of the coordinate transforms allows a number of possible perspectives to be computed and processed in an indexing step. This is achieved by indexer 306 of input module 324. Indexing of discrete positions thus allows for quick access wherein an operator does not have to go through a complex process of navigating to a desired view. In an example, the operator is enabled to position the reconstructed 3D model 304 in these predefined orientations and at zoom levels that corresponds to the orientation and size of a single frame 2D or single frame 3D data (2D photo, 2D video image, 3D image) thus providing an enhanced comparison and decision process/workflow. Moreover, the operator may navigate through these orientations by manipulating the reconstructed 3D model 304 which then snaps into the predefined orientations or by stepping through the predefined orientations through the use of a keyboard, a click on the screen with the mouse/3D mouse, a touch screen engagement, etc.

With this optimized workflow of accessing the working view the operator can now provide input on the direct measurement data 308 (2D video images, single 3D data frames, etc.) for the purposes of providing supporting information for the automated proposals e.g. margin, user based selection or weighting of frames to use, training information for automated proposals and selection/weighting of frames for improved proposals in the future, manual inspection and manipulation with a live/delayed feedback and control feature.

In the illustrative embodiment, the proposal generator 318 is a trained model and/or uses predictive analytics or algorithmic models to generate automatic and/or AI-enabled margin proposals using one or more of the direct measurement data 308. In another illustrative embodiment, the direct measurement data 308 are obtained by a trainer 316 through the input module 324. The trainer 316 trains a machine learning model using the direct measurement data 308 to produce workflow recommendations. Due to the direct measurement data 308 being raw unaveraged/complete data, the machine learning model 330 is able to produce more accurate workflow recommendations than recommendations produced using the reconstructed 3D model 304. For example, by using the direct measurement data 308 as input dataset for training, the machine learning model 330 learns from the high-quality data to produce margin line recommendations that are more accurate than margin line recommendations provided using the reconstructed 3D model 304.

Further, in the generation of a proposal or workflow recommendation by proposal generator 318, a weighter 320 may be used in some illustrative embodiments to weight a plurality of direct measurement data 308 according to one or more preferences of an operator. By determining a level of contribution of a whole or portion of each of a plurality of direct measurement data 308, the nature and quality of a proposal is controlled to meet one or specifications. For example, a proposal may be re-computed based on a newly weighted direct measurement data 308.

In a further illustrative embodiment, an operator is enabled by a manual modifier 322 to manually control and modify a rendered 3D representation (reconstructed 3D model 304) of the scanned data in a manual workflow. This can be done, for example, with respect to margin line, geometry, or color by modifying the direct measurement data 308 and obtaining a corresponding live or delayed modification/feedback in the reconstructed 3D model 304.

These illustrative embodiments significantly increase usability through quick and easy navigation to display relevant raw data through indexing (determination) of discrete positions of the 3D model wherein an operator does not have to go through a cumbersome process of manually changing to a view with multiple steps and wherein the viewing direction provides the same orientation of reconstructed 3D model 304 and direct measurement data 308 thus supporting the process of comparison and decision making.

Figure 4:
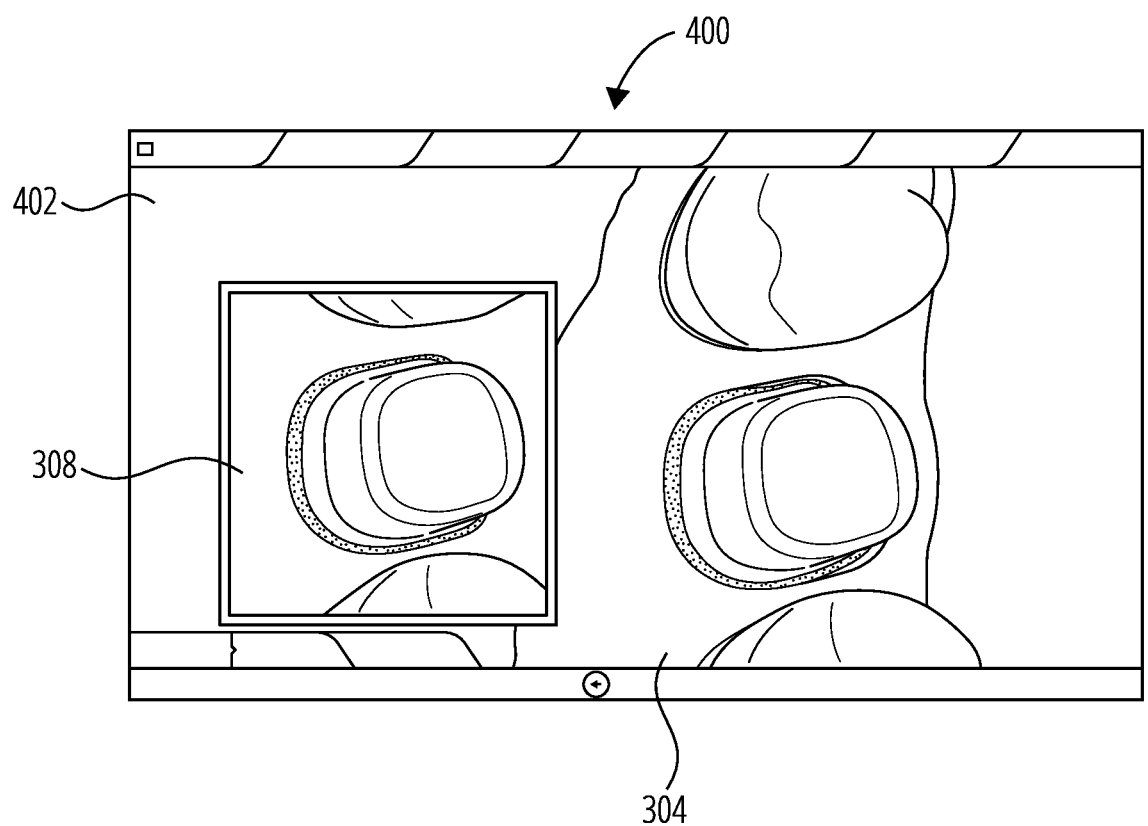
FIG. 4 illustrates an aspect of the subject matter in accordance with one embodiment.

With reference to FIG. 4, this figure depicts an example working view 400 in accordance with an illustrative embodiment. The working view 400 is embodied in application 402 which may be any one of applications 116, 120, 302, depending upon the particular implementation. The working view 400 shows a same perspective of a direct measurement data 308 and a reconstructed 3D model 304, which is shown as a rendered 3D model. This means that both representations have the same orientation and zoom factor (size), thus helping an operator to compare the two representations especially when comparing texture and color.

When the direct measurement data 308 is a single frame 3D data an operator is enabled to modify the perspective. Thus, the orientations and sizes of the single frame 3D data and the reconstructed 3D model 304 change the same way.

Figure 5:
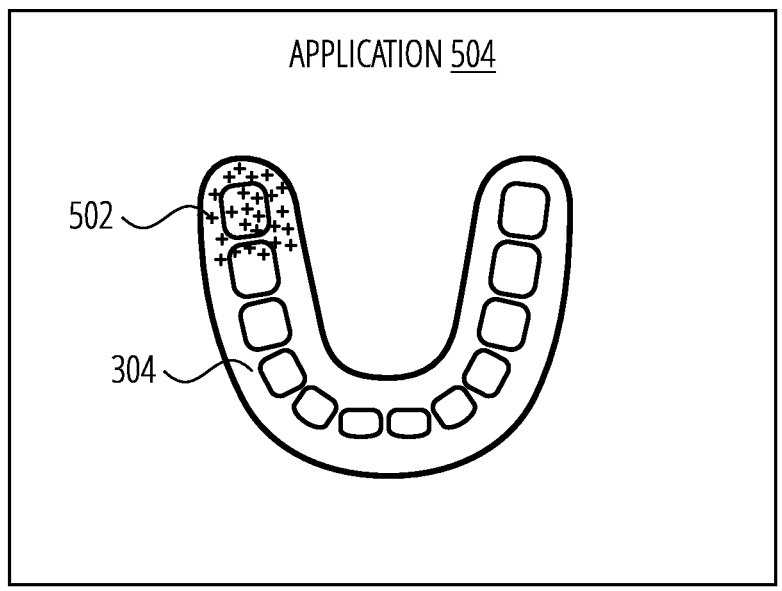
FIG. 5 depicts a sketch of a map representation of possible working views in accordance with an illustrative embodiment.

With reference to FIG. 5, this figure depicts an example application 504 showing a reconstructed 3D model 304 configured for an orientation operation in accordance with an illustrative embodiment. The number of generated direct measurement data 308 determines the number of possible perspectives for a working view 400. In the embodiment, indexer 306 is used in an indexing operation to link each of one or more perspectives of the reconstructed 3D model 304 to a corresponding direct measurement data 308 that is indicative of said one or more perspectives in order to establish a control between them and to provide a paired listing of 3D model perspectives and corresponding direct measurement data 308/single frame images. In the embodiment, the paired listing is provided as one or more pair selections 502, positioned in a sub-portion or whole portion of the reconstructed 3D model 304, that are indicative of a correlation between the pair. For example, a pair selection 502 may be positioned at a 3D point on the reconstructed 3D model 304 corresponding to a center coordinate x,y of the direct measurement data 308; selecting the pair selection 502 in this example thus causes an orientation of the reconstructed 3D model 304, said orientation being relative to the 3D point on the 3D model that corresponds to the center coordinate x,y of the direct measurement data 308, to be displayed alongside the direct measurement data 308. In this example, the visualized orientations and sizes of each member of a selected pair may thus be the same. In cases with many possible discrete orientations the pair may instead be highlighted. In another example, in addition to having an image displayed alongside the model view, an additional map is feasible. Thus, two representations of the 3D model may be present: one as an overview/map and another zoomed-in and properly oriented. In another example, the paired listing may not be visualized as a map but may be visualized as a table or list. Of course these are not meant to be limiting and other ways of visualizing the paired listing are possible based on, for example, an established control between the pairs as well as access to coordinates of the direct measurement data 308 and the 3D points of the reconstructed 3D model 304.

By indexing and mapping the correlated views the operator is provided with the ability to quickly access the working view 400. In an example, a "Snap-In function" is achieved, wherein the reconstructed 3D model 304 can only be turned or moved by dragging the mouse, touchscreen, trackball, touchpad into those orientations which provide a correlated view between direct measurement data 308 and reconstructed 3D model 304. The operator can be assisted by a snap-in feature that activates the nearest possible orientation in a live view mode.

In another example, a "Stepwise function" is achieved wherein the reconstructed 3D model 304 can only be turned or moved into those orientations which provide a correlated view between direct measurement data 308 and reconstructed 3D model 304 by using the keyboard or mouse buttons e.g. the arrow keys or space bar and "stepping" through the neighboring orientations.

Figure 6:
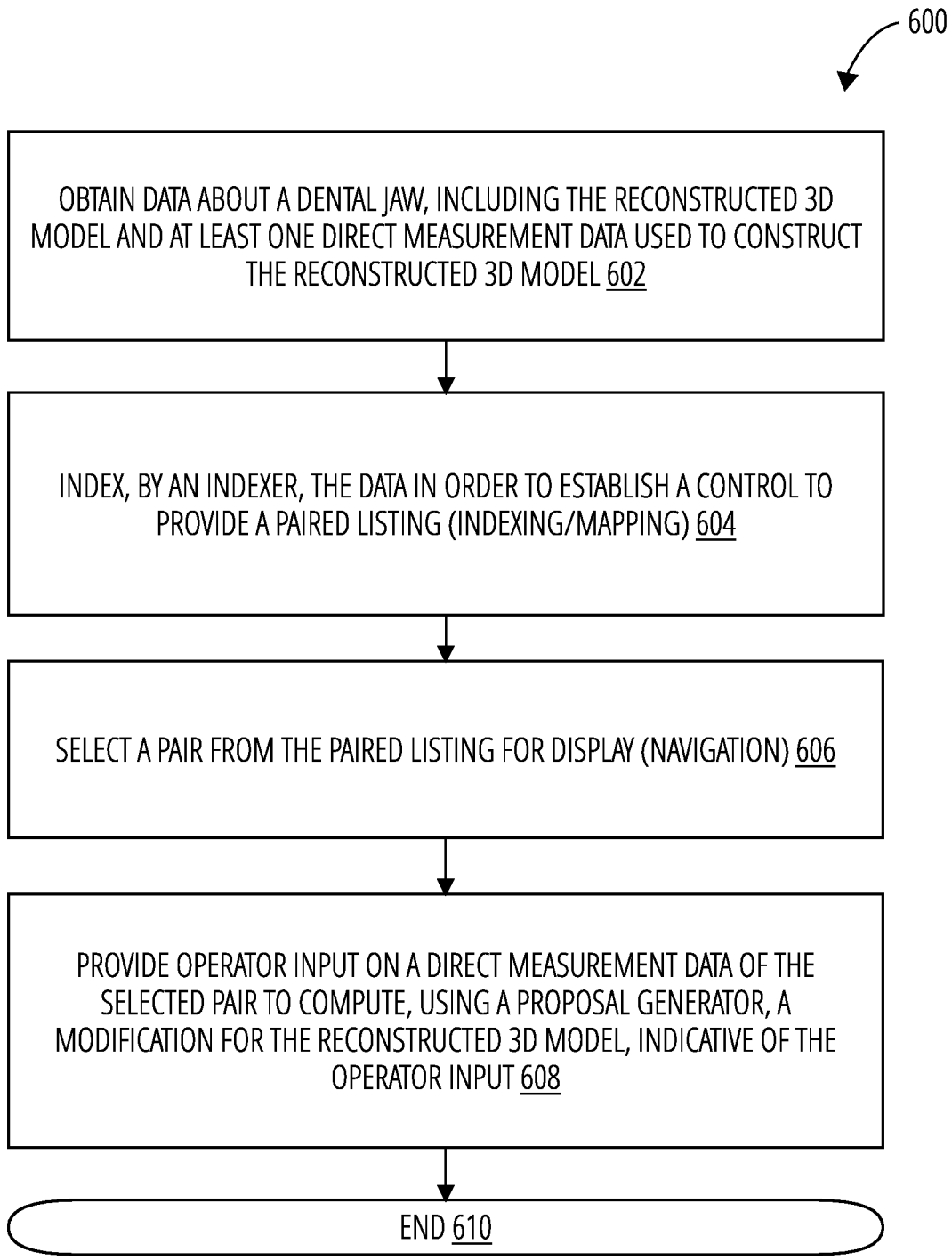
FIG. 6 illustrates a process 600 in accordance with one embodiment.

Turning now to FIG. 6, the figure illustrates a process in which illustrative embodiments may be implemented. The process begins at step 602, wherein data about a dental jaw is obtained. The data includes a reconstructed 3D model 304 of the dental jaw, and at least one direct measurement data 308 used to construct the reconstructed 3D model 304. In step 604, process 600 indexes, by an indexer, the data by linking each of one or more perspectives of the reconstructed 3D model 304 with a corresponding direct measurement data 308 indicative of the one or more perspectives in order to establish a control between them and to provide a paired listing of first virtual 3D model perspectives and corresponding direct measurement data 308. In step 606, process 600 selects a pair from the paired listing for display. In step 608, process 600 provides operator input on a direct measurement data 308 of the selected pair to compute, using a proposal generator, a modification in the first virtual 3D model of the selected pair indicative of the operator input. The computed modification produces a second virtual 3D model that is more accurate than an accuracy of the first virtual 3D model. The process ends at step 610.

In an example of process 600, an operator scans a patient with a dental scanner 122. The geometry and color of a 3D model of the patient's intraoral cavity is calculated. In addition to geometry and color, the perspectives of the 3D model are generated/saved for which a corresponding single 2D/3D image is available (indexing, list, table) and eventually linked to a position on the jaw (mapping). In a particular mode of the application used by the operator, the 3D model can only be moved into those orientations which also display a single corresponding 2D/3D image (navigation).

Figure 7:
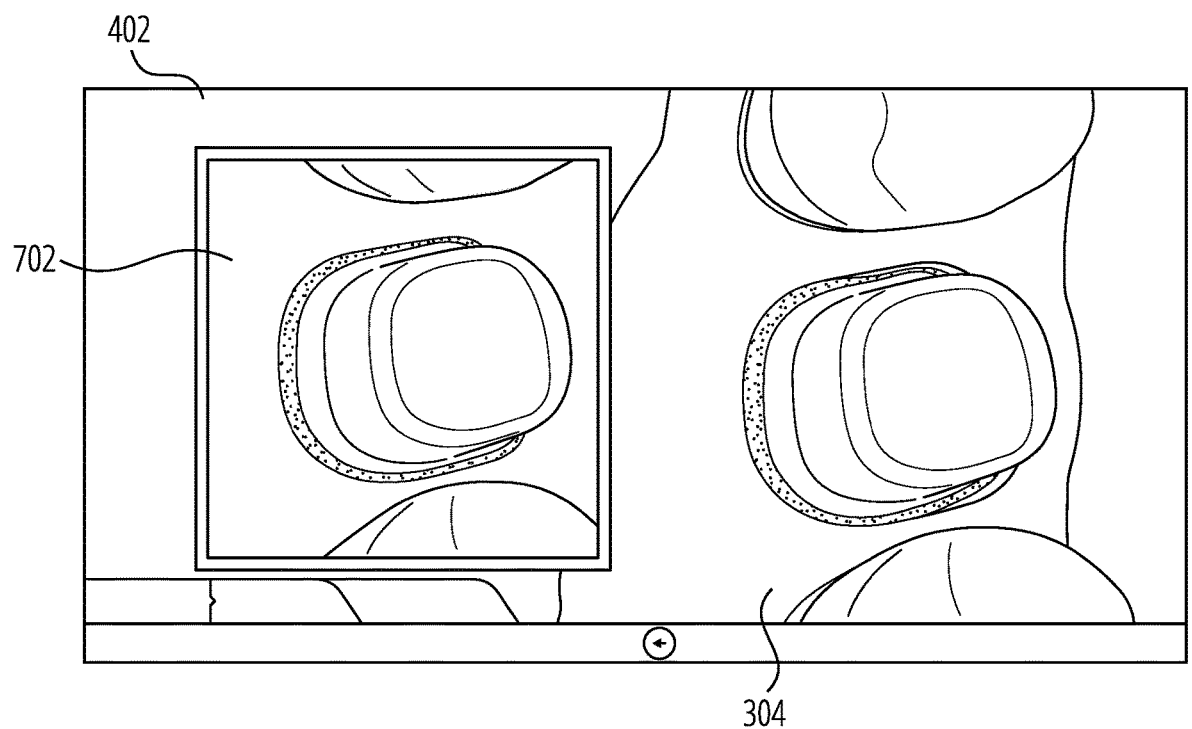
FIG. 7 depicts a sketch of an application in accordance with an illustrative embodiment.

Before the modification step in process 600, step 608, an application such as application 402 optionally uses a single direct measurement data 308 to compute an initial margin proposal (not shown) or other initial workflow recommendation or to improve on an existing margin proposal (or other initial workflow recommendation). FIG. 7 shows an initially selected direct measurement data 702 which is to be used as input for creating an initial automated margin proposal on reconstructed 3D model 304.

Figure 8:
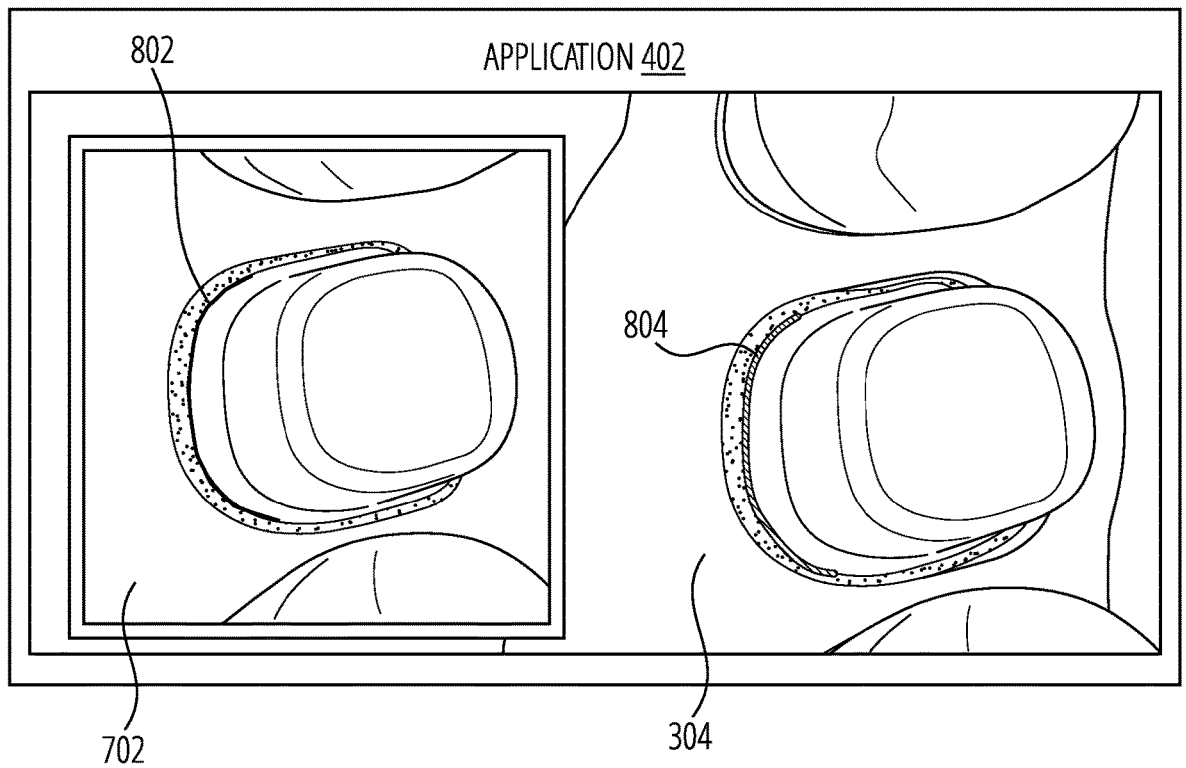
FIG. 8 depicts a sketch of an application in accordance with an illustrative embodiment.

In a subsequent step, the operator may draw, as is shown in FIG. 8, an operator input initial preparation margin 802 on direct measurement data 308, or edit, correct, or manipulate an existing margin proposal from the application 402. Operator input (in this case the operator input initial preparation margin 802) then serves as input for the application 402 to generate, using the proposal generator 318, a new or improved proposed margin line 804. This may be done, for example, using the color information when the direct measurement data 308 is a photo or 2D image, or 3D curvature information for curvature analysis when the direct measurement data 308 is a 3D image. The proposal generator may be a machine learning model or an algorithmic model. For example, the operator input initial preparation margin 802 may be a line drawn by the user or a plurality of single points and information about said operator input initial preparation margin 802 may be used as a guide for the proposal generator 318 to generate an automatic proposal. In the case where the proposal generator 318 is a machine learning model 330, a plurality of operator inputs is used as training data for training the proposal generator 318 in order to take into account specific operator preferences. The process can be repeated for a plurality of perspectives.

The above-mentioned proposal generator can be based, for example, on an artificial machine learning neural network such as a convolutional neural network (CNN). It is a feed-forward artificial neural network which in a classic form consists of a convolutional layer, followed by a pooling layer. The CNN learns by learning free parameters or classifiers of the convolution kernel per layer and their weighting when calculating the next layer. The single 2D images (color, fluorescence, transillumination, absorption) or single 3D frames are used as input to the CNN or machine learning system which was trained using a collection of a large number of single 2D images or single 3D frames. In a further step, the single frame 2D/3D images are analyzed and a relevant output is proposed either on the single 2D images or the 3D model. Any characteristic of the 2D or 3D images can be used as classifiers or features and depend on the input data. In the following some input-output pairs are given for specific 2D/3D single frame images to exemplify possible features. In case the input data are 2D colored images, for example, areas of similar color or color gradient, that belong e.g. to a blue retraction chord, these can be identified as well as areas of a different color, that belong e.g. white/yellow shade of the prepared tooth, which are also identified. In this scenario of an epigingival preparation margin with usage of a retraction chord the output could be a proposal for the margin based on color which is displayed either in the 2D single frame but preferably as a corresponding margin proposal on the 3D model. In case the input data are single 3D frames, regions of high curvature could be identified within the single 3D frames in order to identify the sharpest edge. The output would also result in a margin proposal either in the single 3D frame or preferably as a corresponding margin proposal on the rendered 3D model. In case the input data are 2D UV-fluorescence or IR-transillumination images regions of similar fluorescence areas/transillumination areas could be identified which may correspond to areas with a certain disease such as caries. The output may result in a marked area which proposes tissue infected with caries on the 2D single images or preferably on the rendered 3D model. This information could also contain values for the probability of infection. Another pair of input-output is applicable to all mentioned forms of single 2D/3D images and is a preselection step to select and weight those 2D/3D frames which are likely to deliver the best possible result in the output. The input is a set of 2D or 3D single frames which contain images of the observed region of the dental situation. The output would be a selection of at least one of these 2D/3D single frames which is likely to deliver the best possible result for the outcome. The subset of selected 2D)/3D images can also have weightings or ratings which define the influence on the final result, which again can be e.g. a margin proposal or detection of infectious tissue.

A possible method for training or setting the parameters of the machine learning system consisting of one or more CNN networks is explained below. In a first step, a large number of known 2D or 3D single frames of dental situations are analyzed. Possible input data are generated. The input data are generated in such a way that all possible degrees of freedom are available in the input data. This is achieved using data augmentation. For this purpose, the 2D or 3D single frames of the dental situations are rotated by the specified degrees of freedom and/or scaled along the degrees of freedom. The neural network can advantageously be trained on the basis of a training data set, the training data set including initial 2D or 3D single frames of components and manual changes to these initial 2D or 3D single frames of at least one user. The manual changes can be carried out manually by the user in the 2D or 3D single frames. In this way, the CNN network learns to apply the manual changes made by a specific user to an initial proposal for a proposal such as a preparation margin or tissue infected with caries. The manual changes made by users can be used to train the CNN in order to generate proposals which are adapted to the specific users' preferences. Also, manual changes by different users, connected through a cloud or shared portal can be used to adapt the CNN to make proposals that reflect the proposals of more experienced users.

Further, input data for the CNN and for the training data are not necessarily limited to 2D/3D single frames but can also include rendered 3D models, rendered texture maps and rendered information of infected dental areas. As an example, the input data for the CNN and also for the known training data can consist of a set of single frames and rendered models.

During a workflow, an operator may select weights for a plurality of direct measurement data 308 for use by the proposal generator 318 in generating proposals. Alternatively, the proposal generator is trained in a similar manner to enable automated weighting of direct measurement data 308 for the generation of automated proposals.

Figure 9A:
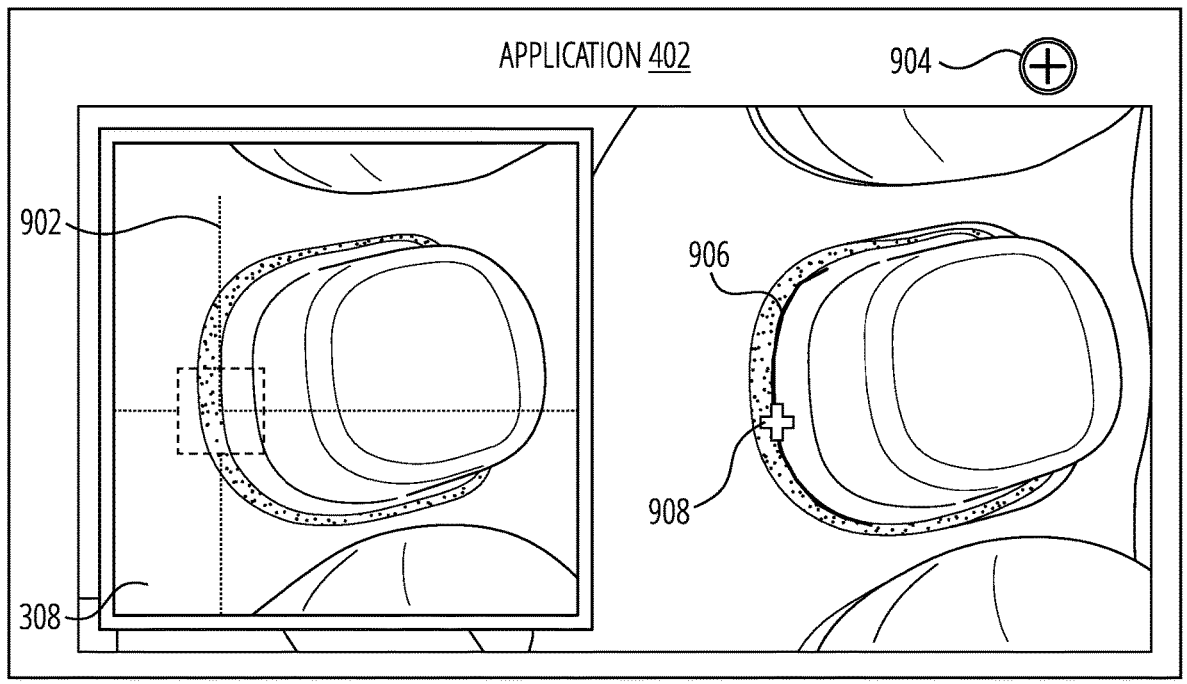
FIG. 9A depicts a sketch of an application in accordance with an illustrative embodiment.
Figure 9B:
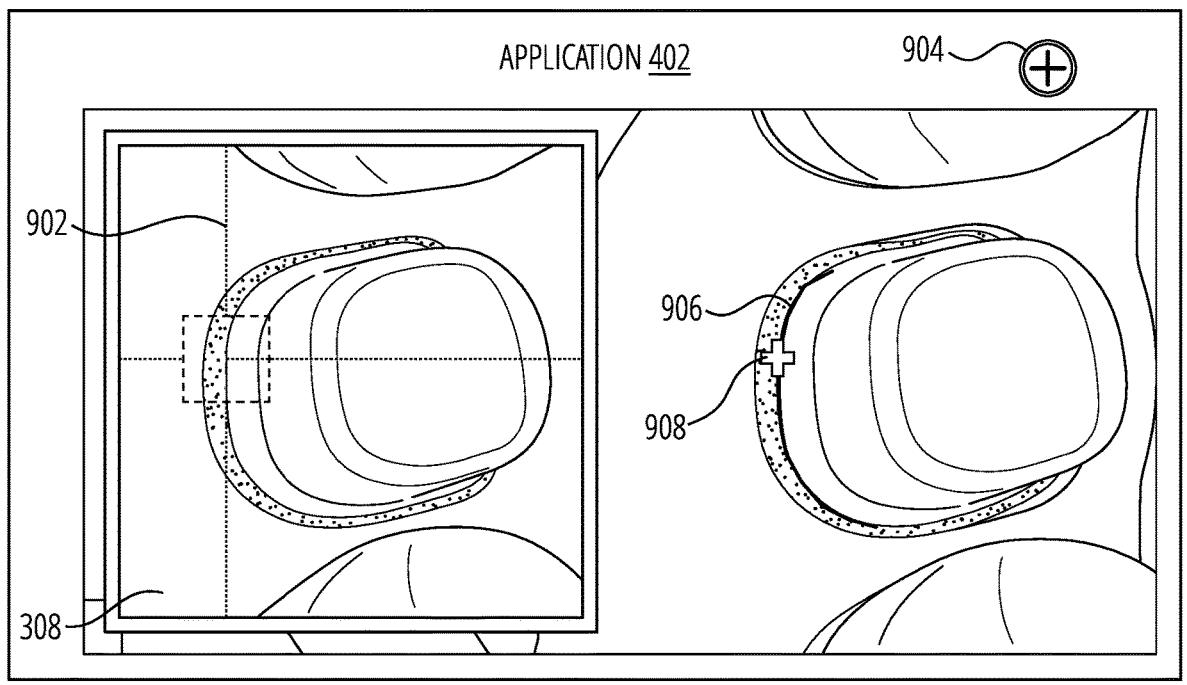
FIG. 9B depicts a sketch of an application in accordance with an illustrative embodiment.
Figure 10:
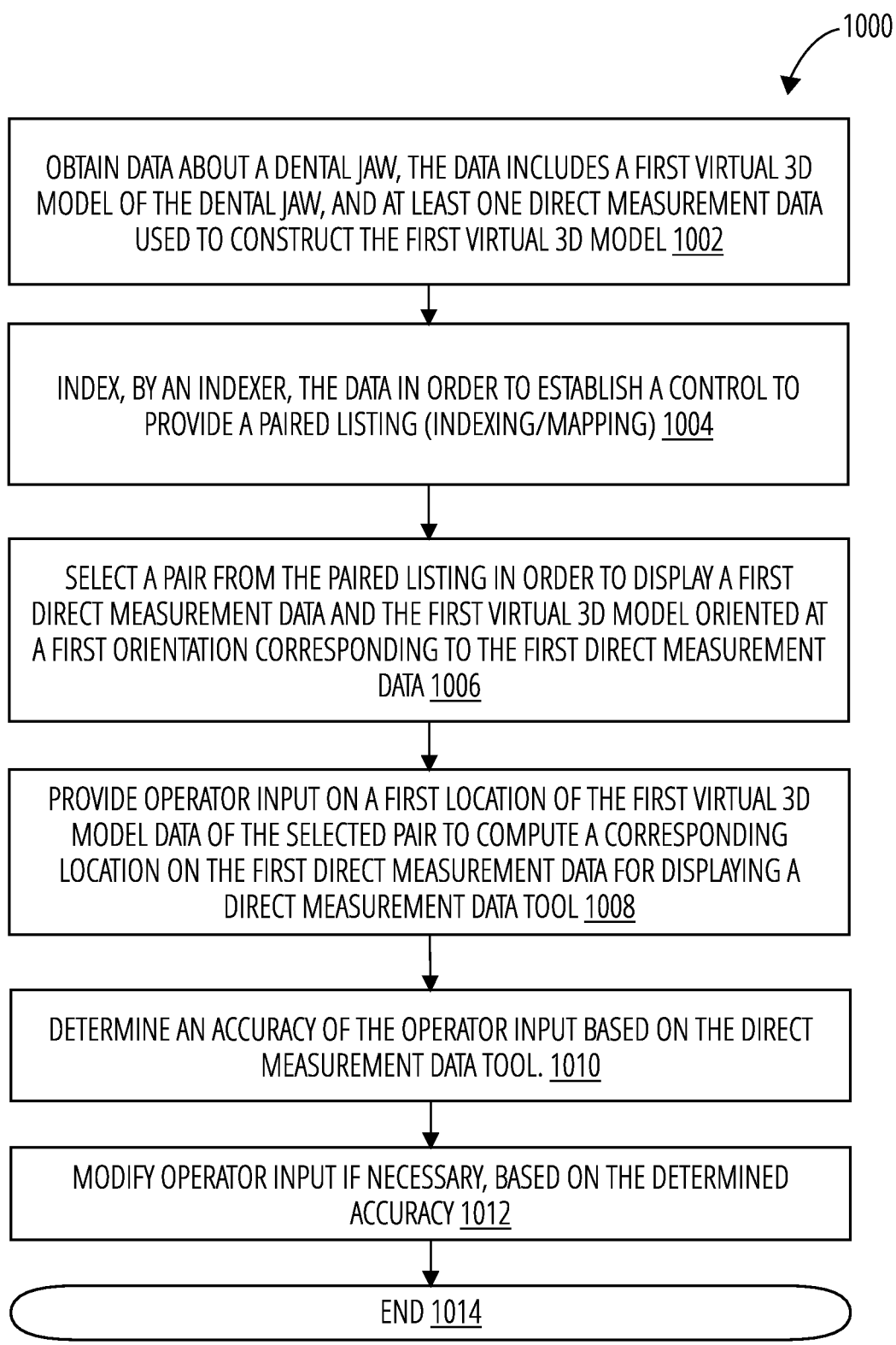
FIG. 10 illustrates a process 1000 in accordance with one embodiment.

In another aspect, due to bi-directional control between the reconstructed 3D model 304 and the direct measurement data 308, along with access to 3D data points of the reconstructed 3D model 304 and coordinates of points in the direct measurement data 308, as well as a global coordinate system of the dental scanner 122, the operator can have a post workflow feedback or a live workflow feedback as explained herein. In the case of a post workflow feedback, the operator may directly manually check, control, or inspect the reconstructed 3D model 304 or a drawn margin by the help of the single images. For example, the operator creates an operator drawn margin line 906 (FIG. 9A, FIG. 9B) or other workflow on the reconstructed 3D model 304. The operator drawn margin line 906 is drawn by the use of a direct measurement data tool 902 such as a "margin finder" on the reconstructed 3D model 304. In the working view the operator then hovers, with a cursor tool 908, over the operator drawn margin line 906 on the reconstructed 3D model 304 and a direct measurement data tool 902 (e.g. a crosshair) appears on the corresponding position of the direct measurement data 308 to check if the margin is at the correct position. The higher quality of information in the direct measurement data 308 compared to information in the reconstructed 3D model 304 allows comparison operations of the operator. The crosshair can consist of two or more crossed lines but can alternatively be designed to enable a better view such as in FIG. 9A and FIG. 9B or a crosshair with a zoom in function to see neighboring data points more clearly. A color of the adjacent data points can be used to ascertain accuracy in an exemplary embodiment.

In another illustrative embodiment, a live workflow feedback is provided wherein the crosshair is displayed in real time as the drawing on the reconstructed 3D model 304 proceeds. Herein the operator draws an operator drawn margin line 906 on the reconstructed 3D model 304. A crosshair is displayed on the direct measurement data 308 to guide the margin drawing process in real time. The crosshair gives immediate position feedback and control while moving a cursor. This helps the operator to decide if the margin will be placed on the correct position.

The workflow feedback is described more generally in process 1000 which begins at step 1002, wherein the process 1000 obtains data about a dental jaw, the data including a first virtual 3D model of the dental jaw/reconstructed 3D model 304, and at least one direct measurement data 308 used to construct the reconstructed 3D model 304. In step 1004, process 1000 indexes, by an indexer, the data by linking each of one or more perspectives of the reconstructed 3D model 304 with a corresponding direct measurement data 308 that is indicative of the one or more perspectives in order to establish a control between them and to provide a paired listing of reconstructed 3D model perspectives and corresponding direct measurement data 308. In step 1006, process 1000 selects a pair from the paired listing in order to display a first direct measurement data and the first reconstructed 3D model 304 oriented at a first orientation corresponding to the first direct measurement data. In step 1008, process 1000 provides operator input on a first location of the first virtual 3D model data of the selected pair to compute a corresponding location on the first direct measurement data for displaying a direct measurement data tool 902. The direct measurement data tool is configured for a viewing or measurement operation that are more accurate than a viewing or measurement operation of the first virtual 3D model, step 1010. This may be due to a higher quality of information in the direct measurement data 308 than a quality of information in the reconstructed 3D model 304 due to averaging effects. The operator input is modified if necessary, based on the direct measurement data tool 902. The processes 1000 ends at step 1014.

Figure 11:
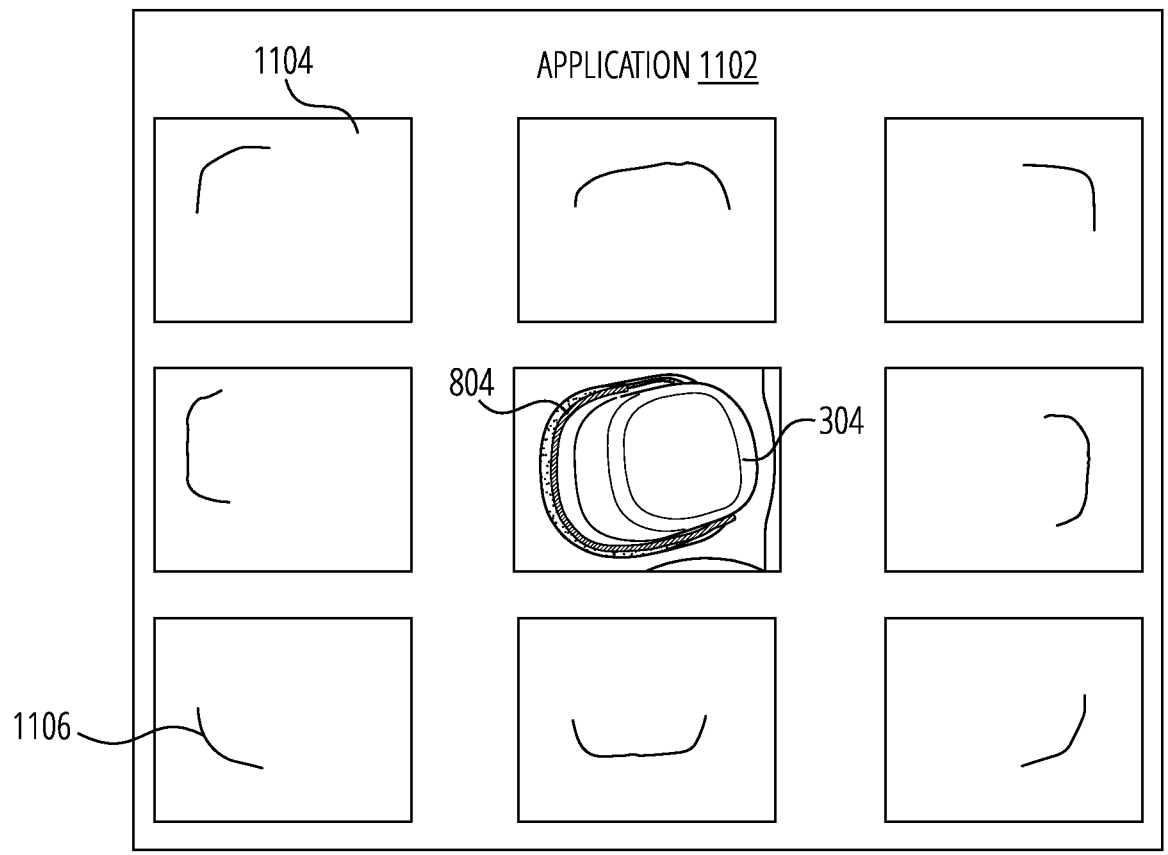
FIG. 11 depicts a sketch of an application in accordance with an illustrative embodiment.

With reference to FIG. 11, the figure depicts another example application 1102 illustrating a simultaneous control view of a complete workflow such as a closed margin. For a given automatic margin proposal, multiple 2D images 1104, each being indicative of a partial margin line 1106 are displayed, which when summed contain all portions of the closed margin. The operator can manipulate the margin in each 2D image 1104 by first selecting the 2D image 1104 wherein a reconstructed 3D model 304 in an orientation corresponding to the selected 2D image 1104, according to an index, is displayed. Operator input is provided for the selected 2D image 1104 as a guide for recalculating the proposed margin line 804. The new calculated proposal is displayed on the reconstructed 3D model 304 after recalculation with the reconstructed 3D model 304 being in an orientation corresponding to the last edited 2D image 1104. In this view the discrete orientations of the reconstructed 3D model 304 may be limited to the depicted 2D images 1104. Of course, other kinds of direct measurement data 308 can be used. The live/post workflow feedback feature can also be implemented in light of the descriptions herein. Further, the operator input can be used as training data for training the proposal generator 318. Moreover other workflows apart from a margin proposal such as workflows involving the editing or manipulation of tooth data, which workflows can be performed using both 3D models and corresponding single frame images in a virtual application, can be achieved in light of the descriptions herein.

Thus, a computer implemented method, system or apparatus, and computer program product are provided in the illustrative embodiments for displaying a single frame control view and other related features, functions, or operations. Where an embodiment or a portion thereof is described with respect to a type of device, the computer implemented method, system or apparatus, the computer program product, or a portion thereof, are adapted or configured for use with a suitable and comparable manifestation of that type of device.

Where an embodiment is described as implemented in an application, the delivery of the application in a Software as a Service (SaaS) model is contemplated within the scope of the illustrative embodiments. In a SaaS model, the capability of the application implementing an embodiment is provided to a user by executing the application in a cloud infrastructure. The user can access the application using a variety of client devices through a thin client interface such as a web browser (e.g., web-based e-mail), or other light-weight client-applications. The user does not manage or control the underlying cloud infrastructure including the network, servers, operating systems, or the storage of the cloud infrastructure. In some cases, the user may not even manage or control the capabilities of the SaaS application. In some other cases, the SaaS implementation of the application may permit a possible exception of limited user-specific application configuration settings.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the dental acquisition unit or user's computer, partly on the user's computer or dental acquisition unit, as a stand-alone software package, partly on the user's computer and partly on a remote computer or entirely on the remote computer or server, etc. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

All features disclosed in the specification, including the claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent, or similar purpose, unless expressly stated otherwise.

What is claimed is:

1. A method comprising the steps of:
   obtaining data about a dental jaw, the data including a first virtual 3D model of the dental jaw, and at least one direct measurement data that is representative of at least a portion of the first virtual 3D model;
   indexing, by an indexer, the data by linking each of one or more perspectives of the first virtual 3D model with a corresponding direct measurement data indicative of said one or more perspectives in order to establish a control between said each of one or more perspectives of the first virtual 3D model and the corresponding direct measurement data and to provide a paired listing of first virtual 3D model perspectives and corresponding single frame images;
   selecting, responsive to the indexing step, a pair from the paired listing for display;
   providing operator input on a direct measurement data of the selected pair to compute, using a proposal generator, a modification in the first virtual 3D model of the selected pair indicative of the operator input;
   wherein the computed modification produces a second virtual 3D model that is more accurate than an accuracy of the first virtual 3D model.

2. The method of claim 1, wherein the at least one direct measurement data is a 2D image that provides information about a feature being selected from the group consisting of an unmodified texture, a visible color, a fluorescence property, a transillumination property, and a reflection or absorption property of the dental jaw when irradiated with visible light, ultraviolet radiation or infrared radiation.

3. The method of claim 1, wherein the at least one direct measurement data is a single frame 3D image that provides information about an unmodified geometry of the dental jaw.

4. The method of claim 1, wherein the computed modification is a change in geometry or color of a part of the first virtual 3D model.

5. The method of claim 1, wherein the computed modification is a change in a proposed margin of the first virtual 3D model.

6. The method of claim 1, wherein the paired listing is displayed as a mapping on the first virtual 3D model, as a table or as a list.

7. The method of claim 1, wherein the at least one direct measurement data is a plurality of direct measurement data and a subset of the plurality of direct measurement data is selected and weighted to trigger a recalculation of the modification using at least the selected subset.

8. The method of claim 1, wherein the control is a bi-directional display relationship, wherein the step of selecting one member of the pair causes another member of the pair to be displayed.

9. The method of claim 1, wherein the computed modification is displayed in real-time.

10. The method of claim 1, further comprising the step of:
providing another input on the first or second virtual 3D model, wherein a corresponding live or delayed feedback is provided on a corresponding position on the direct measurement data.

11. The method of claim 1, wherein the step of providing the operator input on a first location of the direct measurement data of the selected pair computes, using the proposal generator, the modification in a corresponding location on the first virtual 3D model to produce the second virtual 3D model.

12. The method of claim 1, wherein the proposal generator is a machine learning model.

13. The method of claim 1, wherein at least one 2D color image and at least one caries image are displayed in a same view.

14. The method of claim 1, wherein a plurality of direct measurement data that are attributable to a same coordinate transformation, are displayed simultaneously.

15. A computer system comprising a processor configured to perform the steps including:
obtaining data about a dental jaw, the data including a first virtual 3D model of the dental jaw, and at least one direct measurement data that is representative of at least a portion of the first virtual 3D model;
indexing, by an indexer, the data by linking each of one or more perspectives of the first virtual 3D model with a corresponding direct measurement data indicative of said one or more perspectives in order to establish a control between said each of one or more perspectives of the first virtual 3D model and the corresponding direct measurement data and to provide a paired listing of first virtual 3D model perspectives and corresponding single frame images;
selecting, responsive to the indexing, a pair from the paired listing for display;
providing operator input on a direct measurement data of the selected pair to compute, using a proposal generator, a modification in the first virtual 3D model of the selected pair indicative of the operator input;
wherein the computed modification produces a second virtual 3D model that is more accurate than an accuracy of the first virtual 3D model.

16. The computer system of claim 15, wherein the computed modification is a change in a proposed margin of the first virtual 3D model.

17. A non-transitory computer-readable storage medium storing a program which, when executed by a computer system, causes the computer system to perform a procedure comprising the steps of:
obtaining data about a dental jaw, the data including a first virtual 3D model of the dental jaw, and at least one direct measurement data that is representative of at least a portion of the first virtual 3D model;
indexing, by an indexer, the data by linking each of one or more perspectives of the first virtual 3D model with a corresponding direct measurement data indicative of said one or more perspectives in order to establish a control between said each of one or more perspectives of the first virtual 3D model and the corresponding direct measurement data and to provide a paired listing of first virtual 3D model perspectives and corresponding single frame images;
selecting, responsive to the indexing step, a pair from the paired listing for display;
providing operator input on a direct measurement data of the selected pair to compute, using a proposal generator, a modification in the first virtual 3D model of the selected pair indicative of the operator input;
wherein the computed modification produces a second virtual 3D model that is more accurate than an accuracy of the first virtual 3D model.

* * * * *